US007627436B2

(12) United States Patent
Park et al.

(10) Patent No.: US 7,627,436 B2
(45) Date of Patent: Dec. 1, 2009

(54) METHOD OF SELECTING OPTIMIZED SNP MARKER SETS FROM MULTIPLE SNP MARKERS ASSOCIATED WITH A COMPLEX DISEASE

(75) Inventors: Kyung-hee Park, Seoul (KR); Kyoung-a Kim, Gwangmyeong-si (KR); Kyu-sang Lee, Suwon-si (KR)

(73) Assignee: Samsung Electronics Co., Ltd. (KR)

( * ) Notice: Subject to any disclaimer, the term of this patent is extended or adjusted under 35 U.S.C. 154(b) by 461 days.

(21) Appl. No.: 11/063,513

(22) Filed: Feb. 23, 2005

(65) Prior Publication Data

US 2005/0192763 A1 Sep. 1, 2005

(30) Foreign Application Priority Data

Feb. 28, 2004 (KR) ..................... 10-2004-0013781

(51) Int. Cl.
*G06F 19/00* (2006.01)

(52) U.S. Cl. ........................................................ 702/19

(58) Field of Classification Search ....................... None
See application file for complete search history.

(56) References Cited

U.S. PATENT DOCUMENTS

2003/0162207 A1 8/2003 Comings et al. ............... 435/6

OTHER PUBLICATIONS

Comings et al. (2001) Clin. Genet. vol. 60, pp. 107-116.*

"Trimming, Weighting, and Grouping SNPs in Human Case-Control Association Studies", Cold Spring Harbor Laboratory Press ISSN 1088-9051/01, 11:2115-2119, Authors: Josephine Hoh, Anja Wille, and Jurg Ott Genome Research (2001)—citation annotated Jan. 1, 2008.

"Mathematical Multi-Locus Approaches to Localizing Complex Human Trait Genes"; Authors: Josephine Hoh and Jurg Ott.; Nature Reviews. Genetics.; pp. 701-709 (2003).

"Methods for Analysis and Visualization of SNP Genotype Data for Complex Dieases"; Authors: Anya Tsalenko, et al.; Pacific Symposium on Biocomputing; pp. 548-561 (2003).

"Trimming, Weighting, and Grouping SNPs in Human Case-Control Association Studies"; Authors: Josephine Hoh, et al.; Genome Research; pp. 2115-2119 (2001).

"Tissue Classification with Gene Expression Profiles"; Authors: Amir Ben-Dor, et al.; Journal of Computational Biology; vol. 7, No. 3/4, pp. 559-583 (2000).

* cited by examiner

*Primary Examiner*—Lori A Clow
(74) *Attorney, Agent, or Firm*—Cantor Colburn LLP

(57) ABSTRACT

Provided is a method of selecting an optimized SNP marker set from a plurality of SNP markers. The method includes selecting an SNP marker set having a high association from a plurality of SNP markers using set-association, selecting SNP markers having a high association by performing discrimination analysis on arbitrary combinations of the markers included in the SNP marker set, and selecting an optimized SNP marker combination satisfying predetermined selection criteria by using receiver operating characteristics (ROC) curve analysis of arbitrary combinations of the selected SNP markers.

8 Claims, 2 Drawing Sheets

METHOD OF SELECTING OPTIMIZED SNP MARKER SETS FROM MULTIPLE SNP MARKERS ASSOCIATED WITH A COMPLEX DISEASE

BACKGROUND OF THE INVENTION

This application claims priority from Korean Patent Application No. 10-2004-0013781, filed on Feb. 28, 2004, in the Korean Intellectual Property Office, the disclosure of which is incorporated herein in its entirety by reference.

1. Field of the Invention

The present invention relates to a method of selecting an optimized SNP marker set having a high association with a specific disease from a plurality of SNP markers.

2. Description of the Related Art

Complex diseases are generated by a plurality of genetic factors. It is known that the generation and development of these complex diseases are affected by a plurality of genes that form a complicated network. Thus, in most cases, one gene or its associated marker does not have a great degree of association with a complex disease, unlike a Mendel's genetic disease, and thus there is a difficulty in diagnosing the complex diseases. That is, it is difficult to find a causative gene or its associated marker to use a diagnosis. If only one known marker associated with a disease is used, an incorrect result of diagnosis may be obtained.

To overcome these problems, there have been attempts to develop and analyze a multiple disease marker. A method of analyzing a haplotype in which markers among various disease markers present in one gene are randomly combined has been developed. However, since only the markers in one gene are analyzed, this method is not suitable for genetic markers dispersed over various genes and chromosomes.

Ott et al. [*Genome Research* 11, 2115, 2001] has developed a set-association method in which relevant statistical information such as allelic association (AA) and Hardy-Weinberg disequilibrium (LD) for multiple SNP markers associated with specific diseases are blended. In the set-association method, highly associated markers can be selected by calculating the product of the two types of statistical information related to association, allelic association and Hardy-Weinberg disequilibrium. In addition, receiver operating characteristics (ROC) curve analysis has been used to evaluate an ability to discriminate case individuals from control individuals. However, these methods have not been used to select optimized SNP markers associated with complex diseases.

SUMMARY OF THE INVENTION

The present invention provides a method of efficiently selecting an optimized SNP marker set from a plurality of SNP markers associated with a specific disease.

According to an aspect of the present invention, there is provided a method of selecting an optimized SNP marker set from a plurality of SNP markers, comprising:

selecting an SNP marker set having a high association from a plurality of SNP markers using set-association;

selecting SNP markers having a high association by performing discrimination analysis on arbitrary combinations of the markers belonging to the selected SNP marker set; and selecting an optimized SNP marker combination satisfying predetermined selection criteria by using receiver operating characteristics (ROC) curve analysis of arbitrary combinations of the selected SNP markers.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

Figure 1:
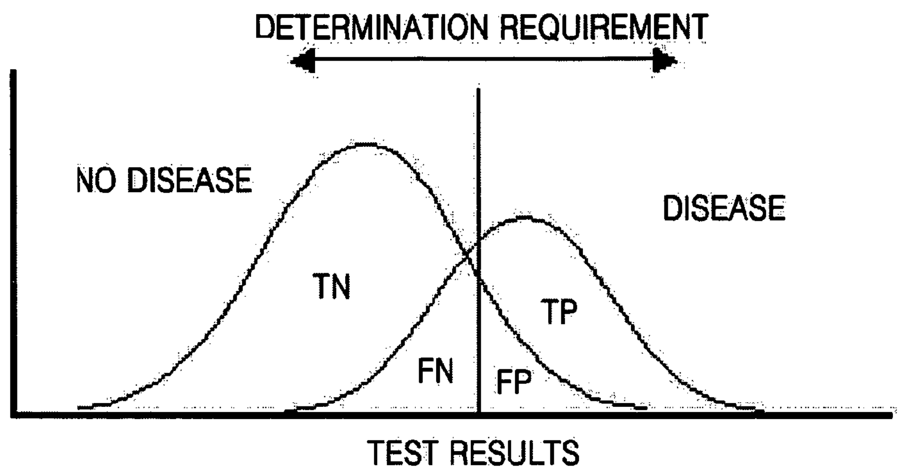
FIG. 1 is a graph illustrating overlapping distribution of the test results.

The present method provides a method for selecting an optimized SNP marker set from multiple SNP markers. The method is used to discriminate the presence or absence of a specific disease. The method comprises selecting an SNP marker set having a high association from a plurality of SNP markers using set-association;

selecting SNP markers having a high association by performing discrimination analysis on arbitrary combinations of the markers included in the SNP marker set; and selecting an optimized SNP marker combination satisfying predetermined selection criteria by using receiver operating characteristics (ROC) curve analysis of arbitrary combinations of the selected SNP markers.

In an exemplary embodiment of the present invention, the set-association comprises calculating a difference in frequency of occurrence of each SNP marker for cases and controls of an arbitrary SNP marker set to obtain an allelic association $t_i$, ordering the allelic associations so that the allelic association with the highest value has rank 1, such that $S_{(n)}=t_i$ (wherein n represents a rank, and $t_i$ represents the allelic association of the ith SNP marker, which has rank n), calculating Sum $S_{(n)}=S_{(1)}+S_{(2)}+\ldots+S_{(n)}$ for each of n=1 to n=the total number of allelic associations, calculating a p-value (significance) for each sum by permutation test, and estimating a significance from the permutation test to select a marker set having the lowest significance.

That is, a mean difference in frequency of occurrence of each SNP marker for a case and a control is calculated for an arbitrary SNP marker set to obtain the allelic association $t_i$. The allelic association is a value indicating an association of an allele. The obtained allelic associations are ordered such that the allelic association with the highest value has rank 1. Then, each sum up to the nth rank, i.e, Sum $S_{(n)}=S_{(1)}+S_{(2)}+\ldots+S_{(n)}$, is obtained starting from the highest ranking SNP.

A significance, p-value is calculated for each sum by permutation test. The p-value associated with the nth sum is determined in a randomization test, in which the labels "case" and "control" are permuted. The p-value can be computed since the number of possible permutations is very large.

Then, the significance is estimated from the permutation test to select a marker set having the lowest significance.

The set-association approach may be implemented using a computer program, for example, the freely available set association analysis software SUMSTAT™, developed by Josephine Hoh (Yale University, New Haven) and Jurg Otto (Beijing Institute of Genomics, Chinese Academy of Sciences).

In another exemplary embodiment of the present invention, the allelic association may be calibrated to a value weighted by linkage disequilibrium (LD). That is, both allelic association (AA) and linkage disequilibrium (LD) are variables indicating an association between susceptibility genes and SNP markers. The linkage disequilibrium may be expressed, for example, by the $\chi^2$ of deviation from a Hardy-Weinberg equilibrium, which is given by the following equation 1:

Equation 1 (1)

$$x^2 = \sum_i \frac{(O_i - E_i)^2}{E_i}$$

wherein $O_i$ is a Hardy-Weinberg equilibrium of the ith SNP marker, $E_i$ is a real frequency of the ith SNP marker.

Thus, when using the allelic association weighted by the linkage disequilibrium obtained by calculating the product of the allelic association (AA) and the linkage disequilibrium (LD), it appears that it is possible to select an SNP marker set having an improved association. There are two aspects to HWD. Although moderately high values (in affected individuals) are indicative of genetic association to a susceptibility locus, extremely high values indicate problems, for example, genotyping errors. Therefore, to ensure quality control, we trim unusually large HWD values. On the other hand, the linkage disequilibrium (LD) cannot be any more than a variable indicating an association with the susceptibility genes if the susceptibility genes are present in different chromosomes. This makes it possible to efficiently select an SNP marker set having a high association with a specific disease.

Thus, more specifically, in the exemplary embodiment of the present invention, the set-association comprises calculating a linkage disequilibrium (LD) related to deviation of a real frequency of a specific SNP marker from a Hardy-Weinberg equilibrium of the SNP marker and, when the LD exceeds a predetermined value, excluding a relevant SNP marker from the set-association, the LD being given by $$x^2 = \sum_i \frac{(O_i - E_i)^2}{E_i} \quad (1)$$

wherein $O_i$ is a Hardy-Weinberg equilibrium of the ith SNP marker, and $E_i$ is a real frequency of the ith SNP marker, calculating the difference in frequency of occurrence of each SNP marker for cases and controls of an arbitrary SNP marker set to obtain an allelic association $t_i$ and calculating a product of the allelic association $t_i$ and the linkage disequilibrium for each SNP marker to obtain the allelic association weighted by the linkage disequilibrium, ordering the weighted allelic associations so that the allelic association with the highest value has rank 1, such that $S_{(n)}=t_i$ (wherein n represents a rank, and $t_i$ represents the weighted allelic association of the ith SNP marker, which has rank n), calculating Sum $S_{(n)}=S_{(1)}+S(_{2})+ \ldots +S_{(n)}$ for each of n=1 to n=the total number of allelic associations, calculating a p-value for each sum by permutation test, and estimating a significance from the permutation test to select a marker set having the lowest significance.

That is, if the linkage disequilibrium exceeds a predetermined value, a relevant SNP marker is excluded from the subsequent analysis. In particular, values of linkage disequilibrium of SNP marker that exceed an arbitrarily predetermined value are set to zero. By determining "outlying" linkage disequilibrium values and excluding them from the analysis, analytical accuracy may be increased.

Then, for an arbitrary SNP marker set, the product of the allelic association $t_i$ and the linkage disequilibrium is calculated to obtain the allelic association $t_i$ weighted by the linkage disequilibrium.

The weighted allelic associations $t_i$ are ordered so that the allelic association with the highest value has rank 1. That is, the largest $t_i$ has rank 1, and is referred to as $S_{(1)}$, and then the second largest $t_i$ has rank 2, and is referred to as $S_{(2)}$. This process is repeated for n allelic associations, thus ranking all SNP markers and producing $S_{(n)}=t_i$ (where n represents a rank, and $t_i$ represents a weighted allelic association of the ith SNP marker).

The weighted 1 to n allelic associations are summed from the allelic association with rank 1 according to the ranks to obtain each sum, i.e., Sum $S_{(n)}=S_{(1)}+S_{(2)}+ \ldots +S_{(n)}$.

P-value is calculated for each sum by permutation test. The p-value associated with the nth sum is determined in a randomization test, in which the labels "case" and "control" are permuted. The p-value can be computed since the number of possible permutations is very large.

Then, the significance is estimated from the permutation test to select a marker set having the lowest significance.

According to an embodiment of the present invention, association is discriminated, for example, by logistic regression analysis, preferably multiple logistic regression analysis. SNP markers are selected via a regression analysis. The logistic regression analysis and the multiple logistic regression analysis are well known in the art, and they can be conveniently applied using a variety of conventional statistical software or a computer program designed for this purpose. For example, the following multiple logistic regression model may be used:

$$\log\frac{p(y=1 \mid x_1, \ldots, x_i)}{1-p(y=1 \mid x_1, \ldots, x_i)} = \alpha + \beta_1 x_1 + \beta_2 x_2 + \ldots + \beta_i x_i$$

wherein i represents a rank of SNP marker.

According to an embodiment of the present invention, the optimized SNP marker set satisfying predetermined selection criteria are selected using ROC curve analysis of arbitrary combinations of the SNP markers selected using the regression analysis.

As used herein, the "ROC curve analysis" is well known in the art, and is a method of analyzing an association of a specific SNP or SNP set with a specific disease using a curve plotting a true positive rate against a false positive rate at a total expression level for each SNP or SNP set.

As used herein, the "ROC curve analysis" has the meaning generally used in the art. Specifically, referring to FIG. 1, TN means a true negative, FN means a false negative, FP means a false positive, and TP means a true positive. As a result of the experiment, if a true positive measurement is a and a false negative measurement is b in the case of the presence of a disease, and a false positive measurement is c and a true negative measurement is d in the case of the absence of a disease, then sensitivity is given by a/(a+b) and a specificity is given by d/(c+d) (see Table 1).

TABLE 1

| | Disease | Frequency | Disease | Frequency | |
|---|---|---|---|---|---|
| Experimental result | Present | n | Absent | n | Sum |
| Positive | True positive | a | False positive | c | a + c |
| Negative | False negative | b | True negative | d | b + d |
| Sum | | a + b | | c + d | |
| Sensitivity | a/(a + b) | | Specificity | d/(c + d) | |

That is, sensitivity is the probability that the experimental result will be positive in the case of the presence of the disease (a true positive rate expressed in percentage) and specificity is the probability that the experimental result will be negative in the case of the absence of the disease (a true negative rate expressed in percentage). A false positive rate which is plotted along the x-axis of the ROC curve may also be indicated as 1-specificity.

In the ROC curve analysis according to an embodiment of the present invention, the ROC curves are respectively based on 1 through N SNP markers and N is the number of SNP markers included in the SNP maker set selected using the regression analysis and the plotted ROC curve is analyzed to select the optimized marker set.

The criteria for selecting the optimized marker set from the ROC curve may be selected from the group consisting of the number of markers, sensitivity, specificity and area under the ROC curve. The selection criteria may depend on the specific disease or environmental factors. For example, if the SNP marker sets have the same or similar sensitivity and specificity, then those having the smaller number of SNP markers may be selected. Fewer SNP markers, higher sensitivity and wider area under the ROC curve are advantageous.

The present invention will be now described in more detail by presenting examples. These examples are for illustrative purpose, and are not intended to limit the scope of the present invention.

EXAMPLE

Example 1

Screening of Colorectal Cancer-Specific SNP Markers

In Example 1, a plurality of SNP markers were selected from a group of 256 colorectal cancer patients (case) and a group of 296 normal persons (control), and from the selected SNP markers, the optimized SNP marker set associated with colorectal cancer were selected.

In detail, DNA was isolated from blood samples from the cases (256) known to be suffering from colorectal cancer and thus under treatment and the controls (296) having no symptoms of colorectal cancer and the frequency of occurrence of specific single nucleotide polymorphisms was analyzed. The cases and controls were all Korean females, and they were the same age. Among several tens of thousands SNPs selected from a database (realSNP.com), the single nucleotide polymorphisms that were assumed to be associated with the disease were selected, and this association was verified using many experiments. Then, primers with sequences around the single nucleotide polymorphisms were used to analyze single nucleotide sequences in the sample.

1. Preparation of DNA Samples

DNA was extracted from blood samples from the cases and the controls. DNA extraction was performed using a conventional extraction method [Molecular cloning: A Laboratory Manual, p 392, Sambrook, Fritsch and Maniatis, 2nd edition, Cold Spring Harbor Press, 1989] and the instructions for a commercially available kit (Gentra system). Among the extracted DNA, that having purity ($A_{260}/A_{280}$ nm) of at least 1.7 was selected and used in the experiment.

2. Amplification of Target DNA

Target DNA that corresponds to a predetermined DNA region containing an SNP to be analyzed was amplified by a PCR (polymerase chain reaction). The PCR was performed in a conventional manner and the conditions were as follows. First, a target genome DNA was prepared with a concentration of 2.5 ng/ml. Next, a PCR reaction solution containing the following components was prepared:

| | |
|---|---|
| water (HPLC grade) | 2.24 μl |
| 10 × buffer (containing 15 mM $MgCl_2$ and 25 mM $MgCl_2$) | 0.5 μl |
| dNTP mix (GIBCO) (25 mM/each) | 0.04 μl |
| Taq pol (HotStar) (5 U/μl) | 0.02 μl |
| forward/reverse primer mix (1 μM/each) | 1.00 μl |
| DNA (2.5 ng/reaction) | 1.00 μl |
| Total volume | 5.00 μl |

The forward and the reverse primers were selected at suitable loci upstream and downstream from a single nucleotide polymorphism.

The PCR reaction solution was maintained at 95° C. for 15 minutes, and then underwent 45 cycles of being at 95° C. for 20 sec, 56° C. for 30 sec, and 72° C. for 1 minute, and then maintained at 72° C. for 3 minutes before being stored at 4° C. Thus, target DNA fragments containing no more than 200 nucleotides were obtained.

3. Analysis of Single Nucleotide Polymorphisms in an Amplified Target DNA

Analysis of single nucleotide polymorphisms in amplified target DNA was performed using homogeneous MassExtension (hereinafter, referred to as hME) technology (Sequenom). The principle of hME is the following: First, a primer complementary to nucleotides in the target DNA fragment up to a single nucleotide polymorphism to be analyzed (also, referred to as extension primer) is constructed. Next, the primer is hybridized to the target DNA fragment and a DNA polymerization reaction is carried out. A reagent (for example, ddTTP) is added to the DNA polymerization reaction to prevent the reaction from going to completion. The reagent stops the reaction when a nucleotide complementary to a first allelic nucleotide (for example, allele A) in the SNP to be analyzed bonds to the first allelic nucleotide. If the first allelic nucleotide is located in the first position of the SNP to be analyzed, then the product of the reaction includes only a third allelic nucleotide (for example, allele T) complementary to the first allelic nucleotide attached to the primer. However, if a second allelic nucleotide (for example, allele G) in the SNP to be analyzed is located at a position before the first occurrence of first allelic nucleotide, then the product of the reaction includes a fourth allelic nucleotide complementary to the first allelic nucleotide. This is true for all allelic nucleotides in the SNP to be analyzed that occur before the first occurrence of the first allelic nucleotide. Thus, the final product of the reaction will include the third allelic nucleotide only once outside the primer, and this allelic nucleotide will be located at the last position of the product. The length of the product from the end of the primer is determined using mass spectroscopy, and thus a location of one of the first allelic nucleotides in the target DNA can be determined. Specific conditions of the experiment are as follows:

First, free dNTP was removed from the PCR product. For this, 1.53 μl of pure water, 0.17 μl of HME buffer, and 0.30 μl of SAP (shrimp alkaline phosphatase) were introduced into a 1.5 ml tube and mixed to prepare an SAP enzymatic solution. The SAP enzymatic solution was centrifuged in the tube at 5000 rpm for 10 seconds. Then, the PCR product was introduced in the tube. The tube was sealed and maintained at 37° C. for 20 minutes and then at 85° C. for 5 minutes, and stored at 4° C.

Next, the homogeneous MassExtension was carried out using the target DNA product as a template. The reaction mixture contained the following components:

| | |
|---|---|
| water (nano grade of pure water) | 1.728 μl |
| hME extension mix (10 × buffer containing 2.25 mM d/ddNTPs) | 0.200 μl |
| extension primer (100 μM/each) | 0.054 μl |
| Thermosequenase (32 U/μl) | 0.018 μl |
| Total volume | 2.00 μl |

After being uniformly mixed, the reaction mixture was spin-down centrifuged. The tube or plate containing the reaction mixture was tightly sealed, and then maintained at 94° C. for 2 minutes and subjected to 40 cycles of being at 94° C. for 5 sec, 52° C. for 5 sec, and 72° C. for 5 sec before being stored at 4° C. The product of homogeneous MassExtension thus obtained was washed with a resin (SpectroCLEAN).

A sequence in a polymorphism region of the obtained extension product was analyzed using MALDI-TOF (Matrix Assisted Laser Desorption and Ionization-Time of Flight). In the MALDI-TOF method, the flight time of a sample together with an ionized matrix to the detector in the opposite side in a vacuum after a laser beam has been fired onto the sample is determined for mass analysis. The lighter the mass of the sample is, the faster the sample reaches the detector. Based on the mass difference and the known sequence of single nucleotide polymorphisms, the sequence of a single nucleotide polymorphism in the target DNA can be determined.

By determining the sequence of the polymorphism region in the target DNA using MALDI-TOF, 61 SNP markers were obtained. For each individual, each allele can be present in a homozygote or a heterozygote. However, for a population, the ratio of the frequency of homozygotes and the frequency of heterozygotes cannot exceed a statistically significant level. According to Mendel's Law of Heredity and Hardy-Weinberg's law, the frequency of alleles in a population is constant, and if the frequency alleles is statistically significant, it can have a biological functional meaning. According to an embodiment of the present invention, single nucleotide polymorphisms also occur in patients having colorectal cancer at a statistically significant level and thus, can be used for the diagnosis of colorectal cancer and so on.

Example 2

Screening of the Optimized SNP Marker Set

In Example 2, the optimized SNP marker set having highest sensitivity, lowest specificity or largest area under the ROC curve were screened for the 61 colorectal cancer-specific SNP markers selected in Example 1.

(1) Selection of the Optimized SNP Marker Set Using Regression Analysis and ROC Curve Analysis of a Separate SNP Marker (Conventional Method)

First, accuracy was analysed for on SNP marker. The multiple logistic regression and the ROC curve analysis were performed on each of 61 SNP markers, and the results showed that, for the SNP marker having the highest accuracy among the single markers, (specificity, sensitivity)=(0.94, 0.61) and area under the ROC curve=0.779.

Second, the separate markers were ranked on the basis of association with the disease and then, starting from the SNP marker having rank 1, each SNP marker was added sequentially so that a combination of markers (multiple marker), composed of at least one marker, was constructed. For each combination, multiple logistic regression analysis and ROC curve analysis were carried out. The results showed that the best combination was composed of 23 SNP markers from rank 1 to rank 23 and had (specificity, sensitivity)=(0.80, 0.88), and area under the ROC curve=0.928. However, as the number of the markers used in the combination increased, information loss when removing a missing value of data to implement multiple regression analysis become higher and the calculation time became longer. Thus, it is assumed that analysis using a combination composed of the minimum number of markers may reduce the occurrence of missing values and increase the efficiency of the calculation.

(2) Selection of the Optimized SNP Marker Set Using Set-association, Regression Analysis and ROC Curve Analysis The results of selecting the optimized SNP marker set according to an embodiment of the present invention are as follows. First, the set-association was used to select a combination of 5 markers, before performing the multiple logistic regression analysis. The set-association approach was implemented using a commercially available computer program, Sumstat. Thus, the multiple logistic regression analysis and the ROC curve analysis were performed for the respective cases in which the number of the markers is no more than 5.

The results showed that the SNP marker combination including 5 SNP markers had relatively accurate results of (specificity, sensitivity)=(0.93, 0.67), and area under the ROC curve=0.9. These analyses confirmed that the marker set composed of 5 markers had better results than those of a single marker and had substantially similar sensitivity, specificity and area under the ROC curve to the marker set composed of 23 markers. Thus, since the use of 5 SNP markers may provide results similar to those of 23 SNP markers, the marker set composed of 5 markers was selected as the optimized SNP marker set in this Example.

Figure 2:
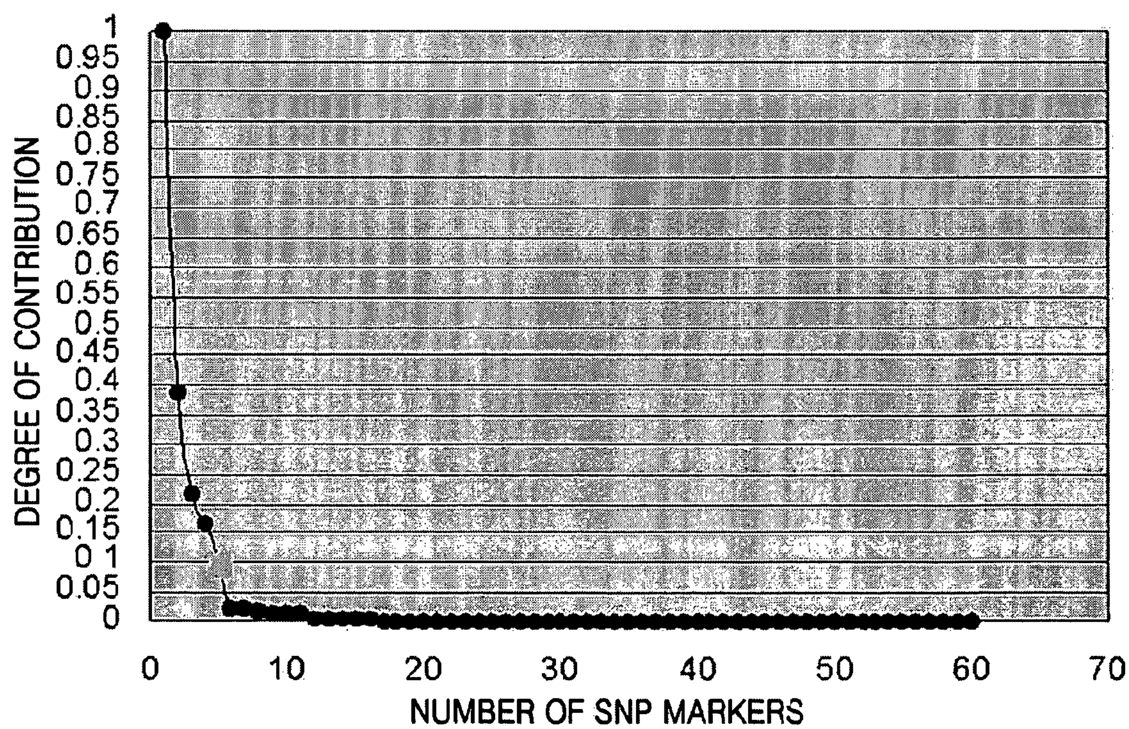
FIG. 2 is a graph illustrating a degree of contribution of each SNP markers with respect to the number of SNP markers.

FIG. 2 is a graph illustrating the result of selecting 5 SNP markers applying the set-association to each of 61 SNP markers. Referring to FIG. 2, allelic associations were obtained for each 61 of SNP markers and then the obtained allelic associations were ordered so that the one with the highest value had rank 1, such that $S_{(n)}=t_i$ (wherein n represents a rank, and $t_i$ represents the allelic association of the ith SNP marker, which has rank n). Next, Sum $S_{(n)}=S_{(1)}+S_{(2)}+\ldots+S_{(n)}$ was calculated, which is the sum of allelic associations from rank 1 to rank n. Then, a degree of contribution ($S_i$/Sum $S_{(n)}$) of each SNP marker was calculated by dividing an allelic association ($S_i$) corresponding to a given rank by the sum (Sum $S_{(n)}$) of allelic associations corresponding to from rank 1 to the given rank. FIG. 2 is a graph illustrating the degree of contribution with respect to the number of the SNP markers. Referring to FIG. 2, while the degree of contribution of SNP marker ranked 5 (■) was 9.7%, that of SNP marker ranked 6 was much less at 2.4 %. That is, an inflection point appeared at rank 5. Thus, a combination of SNP markers up to rank 5 was selected.

Figure 3:
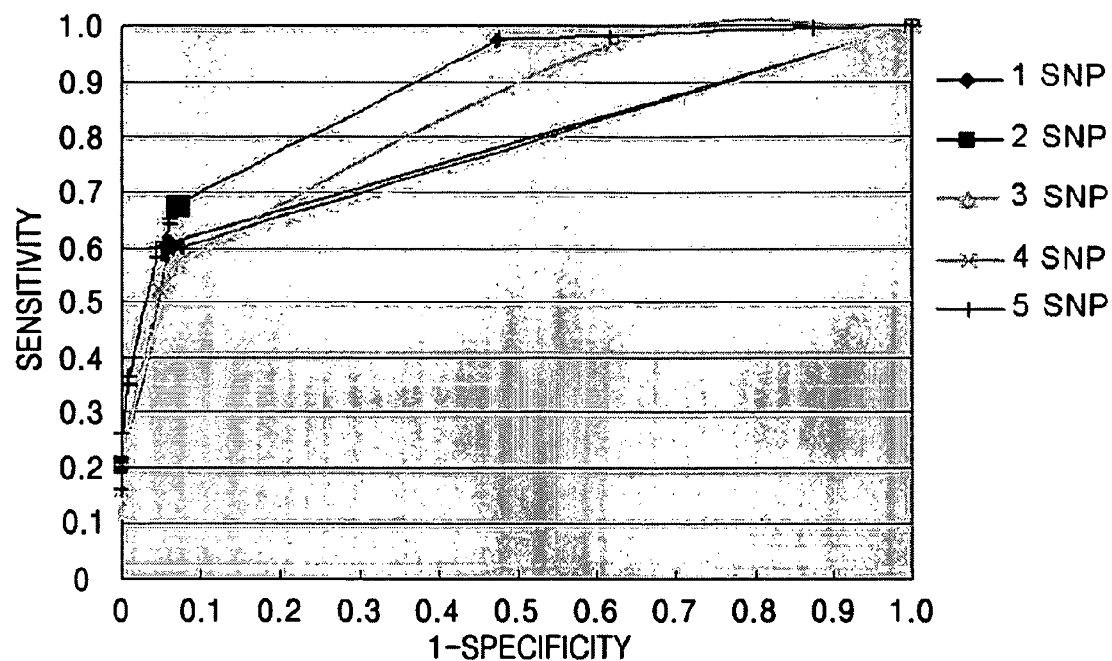
FIG. 3 is a graph illustrating ROC curves for combinations of SNP markers.
Figure 4:
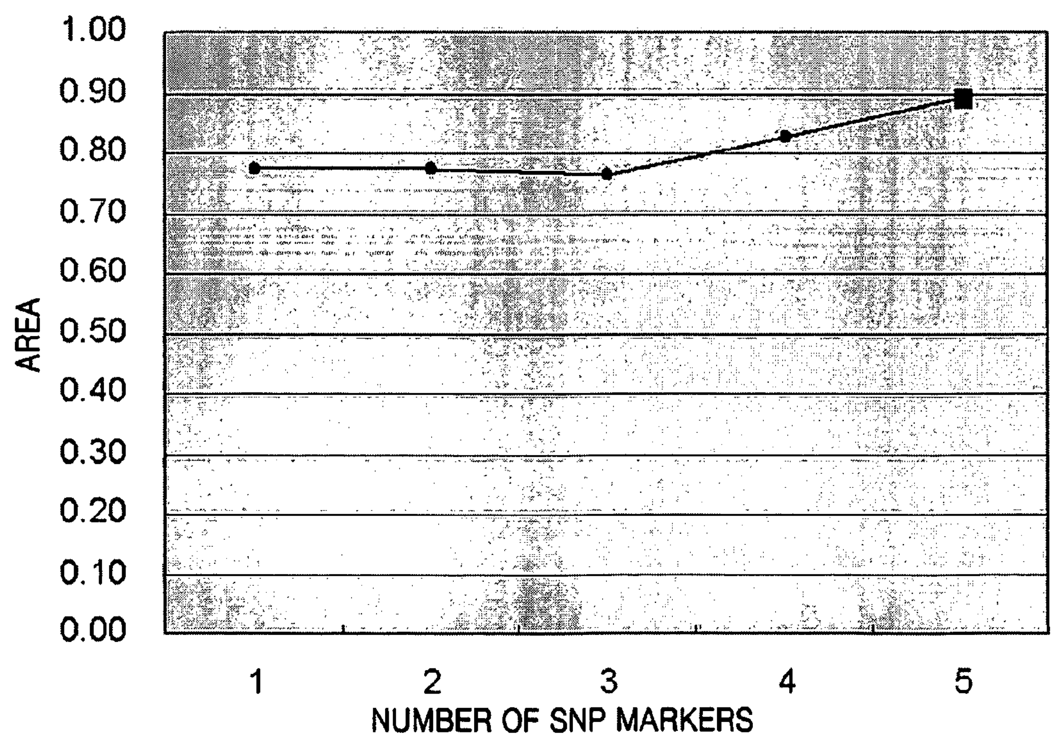
FIG. 4 is a graph illustrating areas under the ROC curve for combinations of SNP markers.

FIGS. 3 and 4 illustrate the results when the SNP marker set was composed of up to 5 SNP markers using the set-association, the multiple regression analysis and the ROC curve analysis.

Discrimination analysis of the selected combination of 5 SNP markers was performed using the multiple logistic regression analysis to discriminate between cases and controls. For this, the following multiple logistic regression model was used:

$$\log\frac{p(y=1\mid x_1,\ldots,x_i)}{1-p(y=1\mid x_1,\ldots,x_i)}=\alpha+\beta_1x_1+\beta_2x_2+\ldots+\beta_ix_i$$

wherein i is a rank of SNP marker.

In this Example, there were six regression coefficients (α, β1 through β5: parameters to be estimated). When applying this statistical analysis tool to the multiple logistic model of the combination of 5 SNP markers, discrimination analysis can be performed by estimating a regression coefficient and a posterior probability. It is possible to determine to which category a new observed value belongs according to the classification criteria of the posterior probability. For example, when using a cutoff posterior probability of 0.58, if the posterior probability is less than 0.58 as a result of the analysis of a combination of 5 SNP markers for a new sample, the sample will be classified as a control, and if the posterior probability is more than 0.58, the sample will be classified as a case. Sensitivity and specificity were calculated according to various posterior probabilities, while increasing the number of markers from 1 to 5 in sequence. The two values thus obtained were used to plot an ROC curve and the area under the ROC curve was analyzed. Thus, estimated accuracy of the SNP marker combination was analyzed.

FIG. 3 shows the results of ROC curve analysis of the SNP marker set composed of 5 SNP markers selected by the set-association. FIG. 4 illustrates the areas under the five ROC curves illustrated in FIG. 3.

According to the present method of selecting an optimized SNP marker set, it is possible to select from a plurality of SNP markers specific to a disease caused by a plurality of genes the optimized SNP marker set having the highest association with the disease.

What is claimed is:

1. A method of selecting a SNP marker set to discriminate presence or absence of a disease in a subject, comprising:

amplifying and determining sequences of a plurality of SNPs in DNA samples from a case population having a disease and from a control population and determining a plurality of SNP markers associated with the disease;

selecting a maximum number of SNP markers from the plurality of SNP markers associated with the disease for a SNP marker set to discriminate presence or absence of the disease in a subject by;

calculating for each SNP marker in the plurality of SNP markers a difference in frequency of occurrence between cases and controls to obtain an allelic association $t_i$;

ordering the allelic associations of the SNP markers so that the allelic association with the highest value has rank 1, such that $S(n)=t_i$, wherein n represents a rank, and $t_i$ represents the allelic association of the ith SNP marker, which has rank n;

calculating $\Sigma S(n)=S(1)+S(2)+\ldots+S(n)$ for each SNP marker;

calculating a degree of contribution for each SNP marker, wherein the degree of contribution$=S(i)/\Sigma S(i)$;

selecting a minimum value for the degree of contribution of a ranked SNP marker; and selecting as the maximum number (j) of SNP markers for a SNP marker set the rank i having the smallest degree of contribution greater than the minimum value;

performing discrimination analysis on combinations of the SNP markers consisting of up to j SNP markers; and analyzing each combination by receiver operating characteristics (ROC) curve analysis to determine an area under the curve;

selecting a SNP marker set having the highest association with the disease from the analyzed combinations, wherein the selected SNP marker set is the analyzed combination having the largest area under the curve, the highest sensitivity, the lowest specificity, or the smallest number of SNP markers; and, outputting the selected SNP marker set to a user.

2. The method of claim 1, wherein selecting the maximum number of SNP markers from the plurality of SNP markers for a SNP marker set further comprises:

calculating a linkage disequilibrium (LD) related to $\chi^2$ for deviation of a real frequency of a specific SNP marker from a Hardy-Weinberg equilibrium of the SNP marker and, when the LD exceeds a predetermined value, excluding a relevant SNP marker from the set-association, the LD being given by $$x^2=\sum_i\frac{(O_i-E_i)^2}{E_i}\qquad(1)$$

wherein $O_i$ is a Hardy-Weinberg equilibrium of the ith SNP marker, and

Ei is a real frequency of the ith SNP marker;

calculating a product of the allelic association $t_i$ and the linkage disequilibrium for the ith SNP marker to obtain a weighted allelic association; and wherein the allelic associations ordered are the weighted allelic associations.

3. The method of claim 1, wherein performing discrimination analysis comprises discriminating between a case and a control using multiple logistic regression analysis.

4. The method of claim 1, wherein each of the ROC curves is a plot of a true positive rate against a false positive rate for the case and control populations.

5. The method of claim 4, wherein ROC curves are analyzed for combinations of 1 through j SNP markers.

6. The method of claim 4, wherein the SNP marker set is selected to be the combination determined to have the largest area under the curve, the smallest sensitivity, the smallest specificity, or the smallest number of SNP markers.

7. The method of claim 1, further comprising obtaining allelic frequency of occurrence for the cases and the controls for each SNP marker.

8. The method of claim 7, wherein obtaining allelic frequency of occurrence for the cases and the controls comprises determining genotypes of the cases and controls for each SNP marker.

* * * * *